US00PP28814P3

(12) United States Plant Patent
van den Haak

(10) Patent No.: US PP28,814 P3
(45) Date of Patent: Dec. 26, 2017

(54) ***PHLOX* PLANT NAMED 'APPOTWCE'**

(50) Latin Name: *Phlox paniculata*
Varietal Denomination: Appotwce

(71) Applicant: Jelle van den Haak, Amsterdam (NL)

(72) Inventor: Jelle van den Haak, Amsterdam (NL)

(73) Assignee: Gootjes-Allplant B.V., Schagen (NL)

( * ) Notice: Subject to any disclaimer, the term of this patent is extended or adjusted under 35 U.S.C. 154(b) by 32 days.

(21) Appl. No.: 14/999,214

(22) Filed: Apr. 11, 2016

(65) Prior Publication Data

US 2017/0295695 P1 Oct. 12, 2017

(51) Int. Cl.
*A01H 5/02* (2006.01)

(52) U.S. Cl.
USPC ..... Plt./320

(58) Field of Classification Search
USPC ..... Plt./320
See application file for complete search history.

*Primary Examiner* — Susan McCormick Ewoldt
(74) *Attorney, Agent, or Firm* — C. A. Whealy

(57) ABSTRACT

A new and distinct cultivar of *Phlox* plant named 'Appotwce', characterized by its broadly upright and relatively compact plant habit; freely flowering habit, numerous small red purple-colored flowers; long flowering period; and good garden performance.

2 Drawing Sheets

Botanical designation: *Phlox paniculata.*
Cultivar denomination: 'APPOTWCE'.

BACKGROUND OF THE INVENTION

The present invention relates to a new and distinct cultivar of *Phlox* plant, botanically known as *Phlox paniculata* and hereinafter referred to by the name 'Appotwce'.

The new *Phlox* plant is a product of a planned breeding program conducted by the Inventor in Andijk and Hazerswoude-Dorp, The Netherlands. The objective of the breeding program was to create new compact and vigorous *Phlox* plants with numerous small flowers.

The new *Phlox* plant originated from a cross-pollination in August, 2012 in Andijk, The Netherlands, of a proprietary selection of *Phlox paniculata* identified as code number 047-11-K013-01, not patented, as the female, or seed, parent, with a proprietary selection of *Phlox paniculata* identified as code number 047-08-002, not patented, as the male, or pollen, parent. The new *Phlox* plant was discovered and selected by the Inventor as a single flowering plant from within the progeny of the stated cross-pollination in a controlled environment in Hazerswoude-Dorp, The Netherlands in August, 2013.

Asexual reproduction of the new *Phlox* plant by terminal cuttings in a controlled greenhouse environment in Andijk, The Netherlands since 2014 has shown that the unique features of this new *Phlox* plant are stable and reproduced true to type in successive generations.

SUMMARY OF THE INVENTION

Plants of the new *Phlox* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Appotwce'. These characteristics in combination distinguish 'Appotwce' as a new and distinct *Phlox* plant:

1. Broadly upright and relatively compact plant habit.
2. Freely flowering habit, numerous small red purple-colored flowers.
3. Long flowering period.
4. Good garden performance.

Plants of the new *Phlox* and the female parent selection differ primarily in the following characteristics:

1. Plants of the new *Phlox* are taller than plants of the female parent selection.
2. Plants of the new *Phlox* and the female parent selection differ in flower color as plants of the female parent selection have white-colored flowers.

Plants of the new *Phlox* and the male parent selection differ primarily in growth habit as plants of the new *Phlox* are more uniform than plants of the male parent selection.

Plants of the new *Phlox* can be compared to plants of *Phlox paniculata* 'Early Red', not patented. In side-by-side comparisons, plants of the new *Phlox* and 'Early Red' differ in the following characteristics:

1. Plants of the new *Phlox* are taller than plants of 'Early Red'.
2. Flower petals of plants of the new *Phlox* are broader than flower petals of plants of 'Early Red'.

BRIEF DESCRIPTION OF THE PHOTOGRAPHS

The accompanying photographs illustrate the overall appearance of the new *Phlox* plant showing the colors as true as it is reasonably possible to obtain in colored reproductions of this type. Colors in the photographs may differ slightly from the color values cited in the detailed botanical description which accurately describe the colors of the new *Phlox* plant.

The photograph on the first sheet is a side perspective view of a typical flowering plant of 'Appotwce' grown in a container.

The photographs on the second sheet are close-up views of typical inflorescences (upper photograph) and typical leaves (lower photograph) of 'Appotwce'.

DETAILED BOTANICAL DESCRIPTION

The aforementioned photographs and following observations and measurements describe plants grown during the summer in 15-cm containers in an outdoor nursery in Mijdrecht, The Netherlands and under cultural practices typically used in commercial *Phlox* production. During the production of the plants, day temperatures ranged from 10° C. to 25° C. and night temperatures ranged from 4° C. to 15° C. Plants were pinched five weeks after planting and were 19 weeks old when the photographs and description were taken. In the following description, color references are made to The Royal Horticultural Society Colour Chart, 2007 Edition, except where general terms of ordinary dictionary significance are used.

Botanical classification: *Phlox paniculata* 'Appotwce'.

Parentage:

*Female, or seed, parent*.—Proprietary selection of *Phlox paniculata* identified as code number 047-11-K013-01, not patented.

*Male, or pollen, parent*.—Proprietary selection of *Phlox paniculata* identified as code number 047-08-002, not patented.

Propagation:

*Type*.—By terminal cuttings.

*Time to initiate roots, summer*.—About 12 days at temperatures about 20° C.

*Time to initiate roots, winter*.—About 16 days at temperatures about 20° C.

*Time to produce a rooted young plant, summer*.—About 36 days at temperatures about 18° C.

*Time to produce a rooted young plant, winter*.—About 42 days at temperatures about 18° C.

*Root description*.—Medium in thickness, fleshy; typically white in color, actual color of the roots is dependent on substrate composition, water quality, fertilizer type and formulation, substrate temperature and physiological age of roots.

*Rooting habit*.—Freely branching; dense.

Plant description:

*Plant and growth habit*.—Herbaceous perennial; broadly upright and relatively compact plant habit; overall shape, broadly obovate; low vigor to moderately vigorous growth habit.

*Plant height*.—About 42.6 cm.

*Plant width (spread)*.—About 39.8 cm.

*Lateral branches*.—Quantity: About ten primary lateral branches per plant. Length: About 26.6 cm. Diameter: About 4 mm. Internode length: About 3.6 cm. Strength: Strong. Aspect: Upright to about 37.5° from vertical. Texture and luster: Smooth, glabrous; slightly glossy. Color: Close to 144A.

Leaf description:

*Arrangement*.—Opposite, simple.

*Length*.—About 9.8 cm.

*Width*.—About 3.4 cm.

*Shape*.—Narrowly ovate to elliptic; slightly to moderately carinate.

*Apex*.—Long apiculate.

*Base*.—Truncate.

*Margin*.—Entire; very finely serrate, inconspicious.

*Texture and luster, upper and lower surfaces*.—Glabrous; slightly rugose; slightly glossy.

*Venation pattern*.—Pinnate.

*Color*.—Developing leaves, upper surface: Close to 137B. Developing leaves, lower surface: Close to 138B. Fully expanded leaves, upper surface: Close to N137A; venation, close to 144A to 144B. Fully expanded leaves, lower surface: Close to 147B; venation, close to 145A.

*Petioles*.—Length: About 3 mm. Diameter: About 2.5 mm by 3 mm. Texture, upper and lower surfaces: Smooth, glabrous. Color, upper surface: Close to 144B; towards the margins, close to N186C.

Flower description:

*Flower type and flowering habit*.—Single rotate and salverform flowers arranged in compound terminal panicles; flowers face upright to outwardly; panicles roughly hemispherical in shape; freely flowering habit with about 280 flowers developing per inflorescence and about 2,800 flowers developing per plant during the flowering season.

*Fragrance*.—Moderately fragrant; sweet, pleasant.

*Natural flowering season*.—Plants begin flowering about nine months after planting; long flowering period, plants flower continuously from July through September in The Netherlands.

*Flower longevity*.—Flowers last about ten days on the plant; flowers not persistent.

*Flower buds*.—Height: About 1 cm. Diameter: About 3.5 mm. Shape: Narrowly obovate. Color: Close to 72B; developing calyx, close to 145C heavily flushed with close to N186C.

*Inflorescence height*.—About 13.4 cm.

*Inflorescence diameter*.—About 14.7 cm.

*Flower diameter*.—About 1.8 cm.

*Flower depth*.—About 1.5 cm.

*Petals*.—Quantity per flower: Typically five in a single whorl; petals fused at the base into a narrow tube; free parts separate to slightly imbricate. Length: Overall, about 1.6 cm; lower fused portion, about 9 mm. Lobe width: About 8 mm. Shape: Free part, spatulate. Apex: Obtuse. Margin: Entire. Texture and luster, upper surface: Smooth, glabrous; moderately velvety; matte. Texture and luster, lower surface: Smooth, glabrous; slightly glossy. Color: When opening, upper surface: Close to N66A; towards the throat, close to N77C; throat, close to N77B. When opening, lower surface: Close to 67C; tube, close to N77B. Fully opened, upper surface: Close to N74A; towards the throat, close to 75C to 75D; throat, close to N77B; color does not change with development. Fully opened, lower surface: Close to N74D and 70B; tube, close to N77B.

*Sepals*.—Quantity per flower: Typically five in a single whorl, fused towards the base; calyx, campanulate. Length: About 8.5 mm. Width: About 1 mm. Shape: Lanceolate. Apex: Narrowly apiculate. Margin: Entire. Texture and luster, upper and lower surfaces: Smooth, glabrous; slightly glossy. Color: When opening and fully opened, upper surface: Close to 145C; towards the apex, close to N186C. When opening and fully opened, lower surface: Close to 145C heavily flushed and tinged with close to N186C.

*Peduncles*.—Length, primary peduncles: About 10.8 cm. Diameter, primary peduncles: About 2.5 mm. Length, secondary peduncles: About 5.6 cm. Diameter, secondary peduncles: About 1.75 mm. Aspect, primary peduncles: Erect. Aspect, secondary peduncles: About 45° from vertical. Strength: Strong. Texture: Smooth, glabrous. Color: Close to 144B; distally, tinged with close to 200B.

*Pedicels*.—Length: About 3.5 mm. Diameter: About 1 mm. Angle: About 40° from the peduncle axis. Strength: Strong. Texture: Smooth, glabrous. Color: Close to 144B; distally, tinged with close to 200B.

*Reproductive organs*.—Stamens: Quantity per flower: Typically five; filaments fused with petals. Filament length: About 0.5 mm. Filament color: Close to N77D. Anther length: About 1 mm. Anther shape: Oblong; basifixed. Anther color: Close to 164C. Pollen amount: Scarce. Pollen color: Close to 11D. Pistils: Quantity per flower: One. Pistil length: About 8 mm. Stigma shape: Cleft, three-parted. Stigma color: Close to 150D. Style length: About 7 mm.

Style color: Close to N77D. Ovary color: Close to 143B.

*Seeds and fruits*.—Seed and fruit development have not been observed on plants of the new *Phlox*.

Garden performance: Plants of the new *Phlox* have been observed to have good garden performance and tolerate rain, wind, high temperatures about 35° C. and to be winter hardy to USDA Hardiness Zone 6.

Pathogen & pest resistance: Plants of the new *Phlox* have been not been observed to be resistant to pathogens and pests common to *Phlox* plants.

It is claimed:

1. A new and distinct *Phlox* plant named 'Appotwce' as illustrated and described.

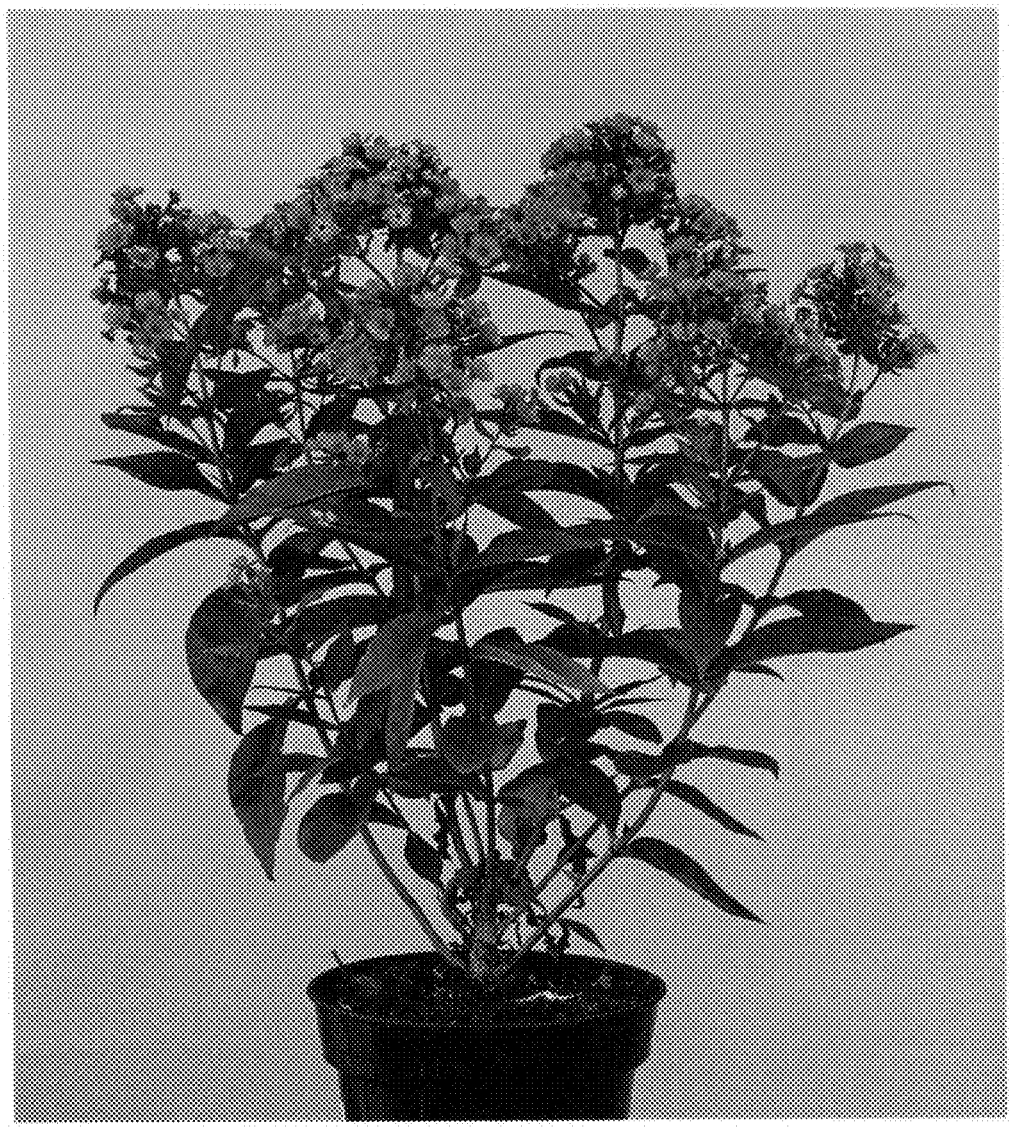

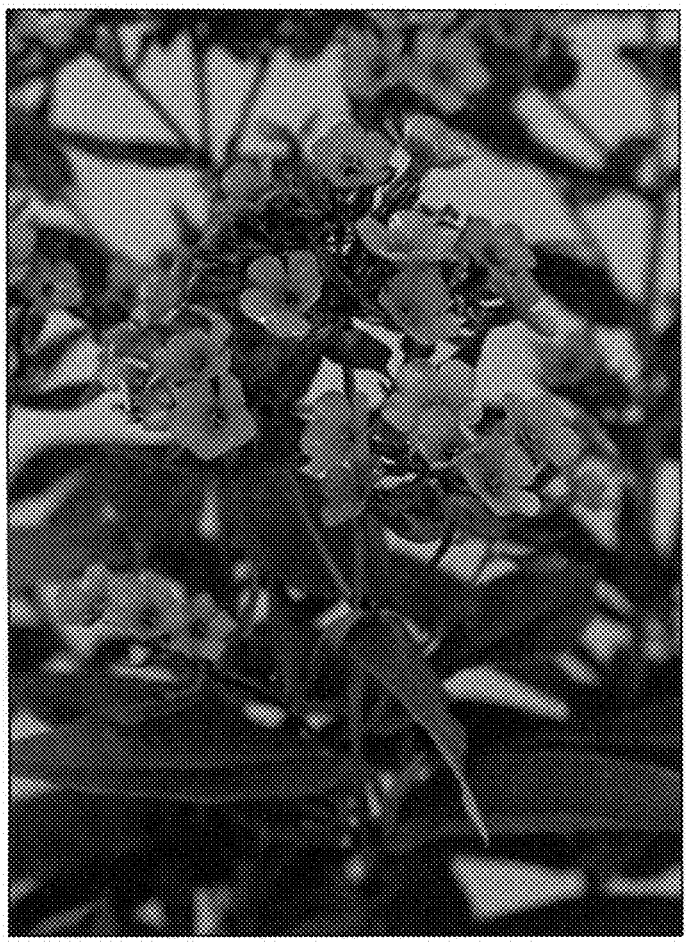
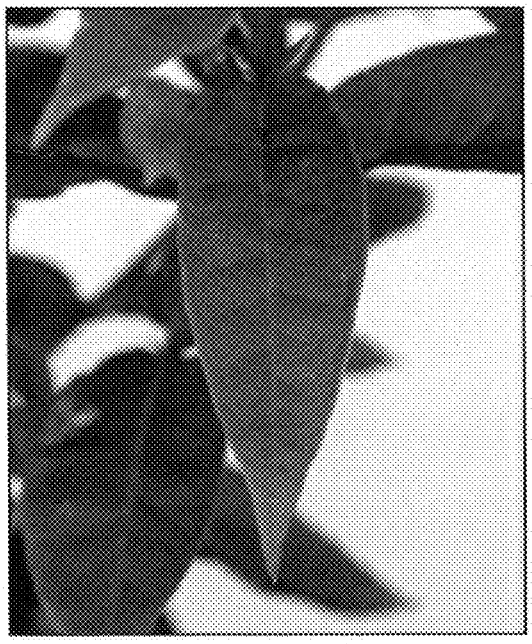

* * * * *